(12) United States Patent
O'Connor et al.

(10) Patent No.: US 9,969,665 B2
(45) Date of Patent: May 15, 2018

(54) ENERGY INTEGRATED CARBON DIOXIDE CONVERSION PROCESS

(71) Applicant: ANTECY B.V., Hoevelaken (NL)

(72) Inventors: Paul O'Connor, Hoevelaken (NL); Timo Roestenberg, Deventer (NL); Saša Marinic, Zeewolde (NL)

(*) Notice: Subject to any disclaimer, the term of this patent is extended or adjusted under 35 U.S.C. 154(b) by 0 days. days.

(21) Appl. No.: 15/036,473

(22) PCT Filed: Nov. 14, 2014

(86) PCT No.: PCT/EP2014/074688
§ 371 (c)(1),
(2) Date: May 13, 2016

(87) PCT Pub. No.: WO2015/071443
PCT Pub. Date: May 21, 2015

(65) Prior Publication Data
US 2016/0289149 A1    Oct. 6, 2016

Related U.S. Application Data

(60) Provisional application No. 61/903,984, filed on Nov. 14, 2013.

(51) Int. Cl.
| | |
|---|---|
| C07C 31/04 | (2006.01) |
| C10G 2/00 | (2006.01) |
| C07C 29/94 | (2006.01) |
| C07C 29/151 | (2006.01) |

(52) U.S. Cl.
CPC .......... C07C 29/1512 (2013.01); C07C 29/94 (2013.01); C07C 31/04 (2013.01); C10G 2/50 (2013.01); Y02P 20/125 (2015.11); Y02P 20/582 (2015.11)

(58) Field of Classification Search
CPC ..... C07C 29/1512; C07C 29/94; C07C 31/04; Y02P 20/582; Y02P 20/125; C10G 2/50
See application file for complete search history.

(56) References Cited

U.S. PATENT DOCUMENTS

| | | | |
|---|---|---|---|
| 2008/0267842 A1 | 10/2008 | Pierson | |
| 2010/0137457 A1* | 6/2010 | Kaplan | ............... C07C 29/1516 518/702 |

FOREIGN PATENT DOCUMENTS

| | | | |
|---|---|---|---|
| DE | 10 2006 034712 A1 | 1/2008 | |
| GB | 2 448 685 A | 10/2008 | |
| WO | WO 2008012039 A2 * | 1/2008 | ........... C07C 29/151 |

(Continued)

OTHER PUBLICATIONS

Dengel, A. et al. Publication No. WO2008/012039A2; Published Jan. 31, 2008, pp. 1-4; English translation.*

(Continued)

*Primary Examiner* — Medhanit W Bahta
(74) *Attorney, Agent, or Firm* — Ramin Amirsehhi LL.M.; David P. Owen

(57) ABSTRACT

An energy integrated process is disclosed for the conversion of carbon dioxide to a liquid product. The conversion reaction is exothermic. The heat of reaction and the heat of condensation of the reaction product or products are used as energy input in a carbon dioxide enrichment step. The enrichment step produces a feed gas for the conversion reaction.

14 Claims, 1 Drawing Sheet

(56) References Cited

FOREIGN PATENT DOCUMENTS

WO    WO 2012168355    6/2012
WO    WO 2013029701 A1 *    3/2013    ............... C10G 2/50

OTHER PUBLICATIONS

Busse, K-H. Publication No. WO2013/029701A1; Published Mar. 7, 2013, pp. 1-11; English translation.*
Hirano, S. et al. Bull. Chem. Soc. Jpn., 68, 1030-1035 (1995).*
Amor, H. B. et al. Chemical Engineering Science 54 (1999) 1419-1423.*
J G Van Bennekom et al—Methanol synthesis beyond chemical equilibrium—Chemical Engineering Science vol. 87 2013 pp. 204-208.

* cited by examiner

ENERGY INTEGRATED CARBON DIOXIDE CONVERSION PROCESS

CROSS REFERENCE TO RELATED APPLICATIONS

This application is a 35 USC § 371 national phase entry of PCT application number PCT/EP2014/074688 filed on Nov. 14, 2014, which claims priority from U.S. application No. 61/903,984 filed on Nov. 14, 2013. Both applications are hereby incorporated by reference in their entireties.

BACKGROUND OF THE INVENTION

1. Field of the Invention

The invention relates generally to process for converting carbon dioxide in an exothermic reaction, and more particularly, to such process whereby energy released in the exothermic reaction is used in a preceding carbon dioxide enrichment step.

2. Description of the Related Art

Prior art processes for converting carbon dioxide to liquid products, such as methanol, are known. Such processes require feed gases having high carbon dioxide content. For this reason such processes generally are integrated with industrial plants that produce gases having high carbon dioxide content, such as power plants, refineries, and the like. Such gases typically contain contaminants, such as $SO_x$, that are corrosive and act as poisons to carbon dioxide conversion catalysts. The feed gases therefore need to be purified before they can be used in the carbon dioxide conversion process.

Carbon dioxide conversion processes, such as the conversion to methanol, are strongly exothermic. Thermal energy must continuously be withdrawn from the carbon dioxide conversion reactor. To avoid energy waste and thermal pollution of the environment, carbon dioxide conversion plants need to be operated in conjunction with other industrial processes having a net energy demand, so that heat generated by the carbon dioxide conversion process can be put to good economic use.

Thus, there is a need for a carbon dioxide conversion process that is sufficiently energy balanced to be operated in stand-alone fashion. There is a further need for a carbon dioxide conversion process that can use feedstock gases that have relatively low carbon dioxide concentration, such as ambient air.

BRIEF SUMMARY OF THE INVENTION

The present invention addresses these problems by providing an energy integrated CO2 conversion process comprising the steps of a. a CO2 enrichment step whereby the CO2 concentration of a feed gas is increased, said enrichment step requiring an energy input;
b. a CO2 conversion step whereby CO2 is converted to a liquid product, said conversion step producing an energy output;
whereby the energy output is used to at least partially offset the energy input.

DETAILED DESCRIPTION OF THE INVENTION

Figure 1:
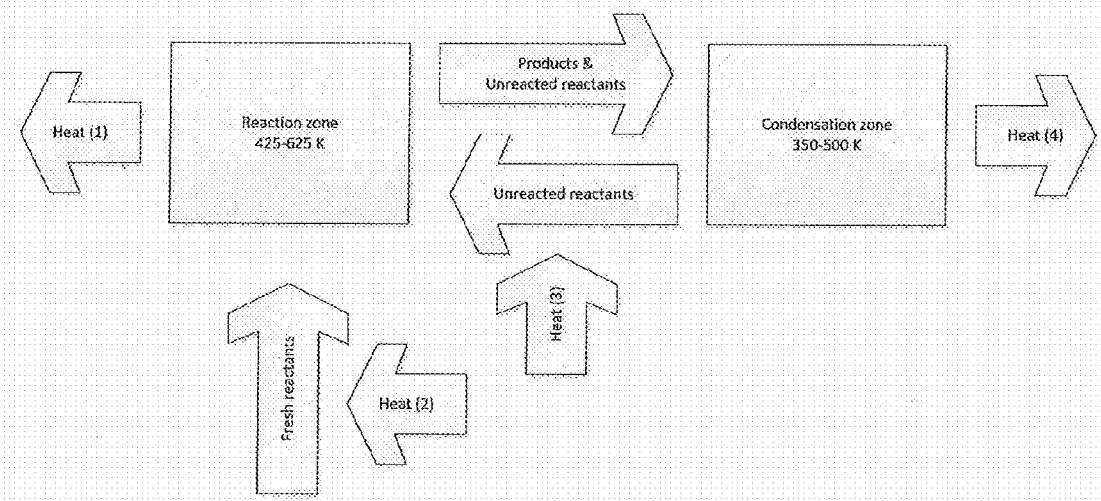
FIG. 1 is a schematic representation of an embodiment of the process according to the invention.

The following is a detailed description of the invention.

Definitions

In its broadest aspect the present invention relates to an energy integrated CO2 conversion process comprising the steps of:
a. a CO2 enrichment step whereby the CO2 concentration of a feed gas is increased, said enrichment step requiring an energy input;
b. a CO2 conversion step whereby CO2 is converted to a liquid product, said conversion step producing an energy output;
whereby the energy output is used to at least partially offset the energy input.

An important aspect of the process of the present invention is the use of a feed gas having low carbon dioxide concentration. In general, any feed gas having a carbon dioxide concentration of less than 50% v/v is suitable for the process. However, the economic advantages of the process are most pronounced when feed gases having much lower carbon dioxide concentrations are used. The process is suitable for use of ambient air as a feed gas. Ambient air currently has a carbon dioxide concentration of about 400 ppm. As ambient air is abundantly available, and substantially free of corrosive contaminants, ambient air is a preferred feed gas for the process of the present invention.

The process comprises a carbon dioxide enrichment step, whereby the carbon dioxide concentration of the feed gas is increased. The carbon dioxide enrichment step requires an energy input.

Examples of carbon dioxide enrichment processes include processes whereby the feed gas is contacted with an absorbent material capable of absorbing carbon dioxide. In a desorption step, absorbed carbon dioxide is released from the absorbent material in a form that is purified relative to the feed gas. Such processes require energy input for contacting the feed gas with the absorbent material, for example using a compressor to force the feed gas through a bed of absorbent material. It will be understood that, the lower the carbon dioxide concentration of the feed gas, the larger the volume of feed gas that must be contacted with the absorbent, and the larger the energy input required.

The desorption step may involve heating the absorbent material, flushing the absorbent material with a flushing gas, applying vacuum to the absorbent material, or a combination of these measures. Whatever method is employed for desorbing carbon dioxide from the absorbent material, energy input will unavoidably be required.

The absorbent material can be any absorbent material for carbon dioxide known in the art. Examples include amines, alkali metal and earth alkaline salts, oxides and hydroxides, and the like. It has been found that salts that absorb carbon dioxide under formation of a bicarbonate are particularly suitable. Sodium and potassium salts, in particular potassium salts, are particularly preferred, in particular sodium and potassium carbonates and hydrates thereof. Highly preferred absorbent materials are disclosed in more detail in our co-pending patent application PCT/EP 2013/065070, the disclosures of which are incorporated herein by reference.

Swing processes have been found to be particularly suitable for enrichment of carbon dioxide-containing feed gases. Examples include temperature swing processes, pressure swing processes, moisture swing processes, and processes using combinations thereof. A preferred method and apparatus, optionally using water vapor as a flushing gas, is disclosed in our co-pending patent application PCT/EP 2013/065074, the disclosures of which are incorporated herein by reference.

The feed gas enriched in carbon dioxide is used in a subsequent carbon dioxide conversion reaction. Particularly preferred for use in the process of the invention is the conversion of carbon dioxide to methanol. A suitable example of this conversion is the thermo-catalytic conversion. Various catalysts have been proposed for this reaction, for example Cu/ZnO/Al2O3. See, for example, a discussion of the history of the industrial use of this reaction in J. G. van Bennekom et al., Chem. Eng. Sci. 87 (2013) 204-208.

The conversion reaction:

$$CO2+3H2 \rightleftharpoons CH3OH+H2O \tag{1}$$

is exothermic, and produces 141 kJ/mole. In addition the process generally includes condensation of the reaction products (methanol and water), which produces 28 kJ mole of methanol, and 39 kJ/mole of water, for a total of 67 kJ/mole of converted CO2.

In an embodiment condensation of methanol takes place in the conversion reactor. This can be accomplished by carrying out the reaction at a relatively high pressure (e.g., 25-175 bar), and by providing one or more condensation zones inside the reactor. The condensation zone or zones are kept at a lower temperature than the reaction zone or zones inside the reactor. For example, the reaction zone or zones may be kept at a temperature in the range of 475K to 575K, and the condensation zones at a temperature in the range of 350K to 400K. It will be understood that the temperature of the condensation zone or zones must be low enough to achieve condensation of methanol. If the reactor pressure is at the high end of the range, for example 175 bar, the temperature of the condensation zone can be kept relatively high, for example 400K. If the reactor pressure is at the low end of the range, for example 25 bar, the condensation zone must be kept at a lower temperature, for example 350K in order to cause condensation of the methanol.

Carrying out condensation of methanol inside the reactor has the important advantage of causing an equilibrium shift. In effect, condensation of methanol causes this reaction product to be withdrawn from the reaction mixture, which shifts the equilibrium of reaction (1) to the right hand side.

In an alternate embodiment unreacted reactants and reaction products are withdrawn from the conversion reactor as a gaseous mixture. The reaction products are separated from this mixture by condensation in a separate vessel. The unreacted reactants are recycled to the conversion reactor.

The integrated process of the invention comprises various heating and cooling steps. For example, step a. may be carried out at temperatures in the range of 250K to 450K. Step a. may involve a temperature swing over a range of 60K to 150K, preferably from 60K to 99K. Step b. may be carried out at a temperature in the range of, for example, 425K to 550K. In general, increasing the temperature of reactants, reaction products and equipment requires an energy input; decreasing the temperature of reactants, reaction products and equipment produces an energy output. The process of the invention aims at capturing the energy outputs as much as possible, and applying them to the required energy inputs.

Key to successful operation of the process of the invention is the significant energy output of step b. It should be noted that step b. is the conversion of CO2 to a liquid reaction product, that is, its energy output comprises the heat of reaction of the conversion, and the heat of condensation of the reaction products. Accordingly, step b. may produce from 100 kJ to 200 kJ per mole of converted CO2.

DESCRIPTION OF ILLUSTRATIVE EMBODIMENTS

The following is a description of certain embodiments of the invention, given by way of example only.

Example 1

FIG. 1 is a schematic representation of an embodiment of the process. The reaction zone and the condensation zone are operated at a relatively low pressure, for example in the range of 25 to 100 bar. The reaction zone and the condensation zone are kept at significantly different temperatures. The reaction zone may be at 425K to 625K; the condensation zone at 350K to 500K. FIG. 1 also represents embodiments in which the condensation is carried out in a separate vessel.

It will be understood that FIG. 1 captures only step b. of the process. The various energy flows are as follows. Heat (1) is the heat of reaction. Heat (2) is the energy required to raise the temperature of the reactants from ambient to the reaction temperature. In many cases carbon dioxide produced in step a. may have a temperature significantly above ambient temperature, so that Heat (2) in those cases is less than is calculated in this example.

Unreacted reactants are recycled from the condensation zone to the reaction zone. Heat (3) represents the energy input required for raising the temperature of the unreacted reactants from the condensation zone temperature to the reaction zone temperature. Heat (4) is the energy output resulting from cooling the reactants and reaction products from the reaction zone temperature to the condensation zone temperature, and the heat of condensation of the reaction products.

The energy balance has been calculated for a reaction zone temperature of 525K and a condensation zone temperature of 375K. The conversion is assumed to be 20% per pass. This means that for every mole CO$_2$ in the fresh reactant stream there are 4 moles of CO$_2$ in the stream of unreacted reactants. For every mole of CO$_2$ in the fresh reactant stream there are 3 moles of H$_2$ in the fresh reactant stream, and 12 moles of H$_2$ in the stream of unreacted reactants.

The heat balance calculations are summarized in Table 1

| Flow | Contributor | Energy (per mole $CO_2$ converted) | Total |
|---|---|---|---|
| Heat (1) | Reaction heat | 141 kJ @525 K | 141 kJ @525 K |
| Heat (2) | Heat capacity $CO_2$, 1 mole, 293 → 525 K | −9.5 kJ @525 K | −37 kJ @525 K |
|  | Heat capacity $H_2$, 3 mole, 293 → 525 K | −27 kJ @525 K |  |
| Heat (3) | Heat capacity $CO_2$, 4 mole, 375 → 525 K | −25 kJ @525 K | −95 kJ @525 K |
|  | Heat capacity $H_2$, 12 mole, 375 → 525 K | −70 kJ @525 K |  |
| Heat (4) | Heat capacity $CO_2$, 4 mole, 525 → 375 K | 25 kJ @375 K | 176 kJ @375 K |
|  | Heat capacity $H_2$, 12 mole, 525 → 375 K | 70 kJ @375 K |  |
|  | Heat capacity $CH_3OH$, 1 mole, 525 → 375 K | 9.2 kJ @375 K |  |
|  | Heat capacity $H_2O$, 1 mole, 525 → 375 K | 5.4 kJ @375 K |  |
|  | Condensation heat $CH_3OH$, 1 mole | 28 kJ @375 K |  |
|  | Condensation heat $H_2O$, 1 mole | 39 kJ @375 K |  |

In Table 1, positive values represent energy outputs, and negative values represent energy inputs. The net energy output of step b. in this example is 141−37−95+176=185 kJ per mole of converted $CO_2$.

Step a. may be a temperature swing absorption/desorption process, whereby $CO_2$ is absorbed from ambient air by potassium sesquihydrate on an active carbon support. Absorption of $CO_2$ involves conversion of the potassium carbonate to potassium bicarbonate, and desorption requires the reverse reaction. The heat of reaction is 41 kJ/mole. The heat capacity of the active carbon support is 900 J/kg*K. The absorption capacity of the absorbent material, which according to literature data is between 1 and 2.5 mole of $CO_2$ per kg, is for the purpose of this calculation assumed to be 1 mole/kg. If the available heat energy from step b. is 185 kJ/mole, the achievable temperature swing is (185−41)/0.9=160K. This is more than sufficient for an absorption/desorption swing process.

Example 2

Figure 2:
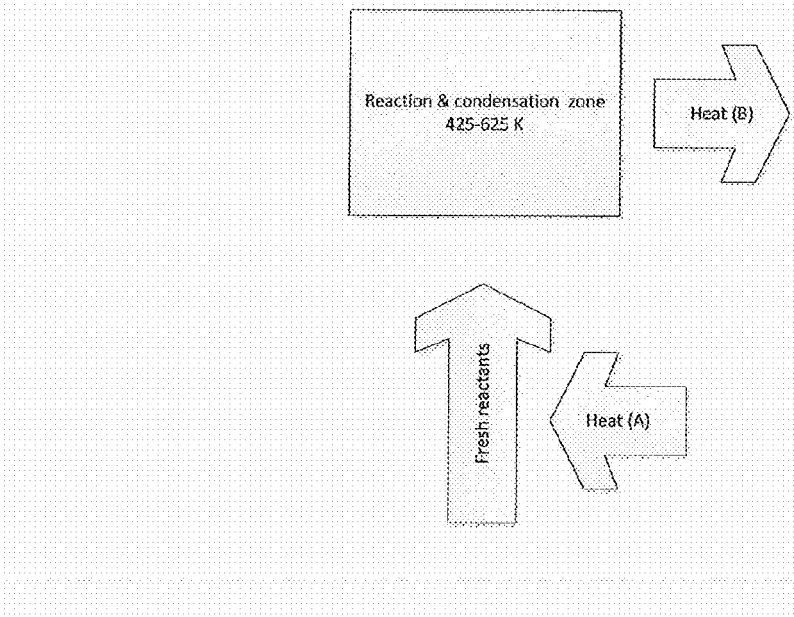
FIG. 2 schematically depicts an embodiment of the process according to the invention in which the reaction zone and the condensation zone are at the same or close to the same temperature.

FIG. 2 schematically depicts an embodiment of the process in which the reaction zone and the condensation zone are at the same (or close to the same) temperature, for example in the range of from 425K to 625K. To accomplish methanol condensation at the reaction temperature, a relatively high pressure is required, for example >150 bar.

Heat (A) is the energy input required for raising the temperature of the reactants from ambient temperature to the reaction temperature. Heat (B) is the energy output resulting from the conversion reaction and the condensation of the reaction products.

The energy balance has been calculated for a reaction temperature of 525K. The one-pass conversion is assumed to be 100% (due to the equilibrium shift resulting from the in situ condensation of methanol). The energy calculations are summarized in Table 2.

TABLE 2

| Flow | Contributor | Energy (per mole $CO_2$ converted) | Total |
|---|---|---|---|
| Heat (A) | Heat capacity $CO_2$, 1 mole, 293 → 525 K | −9.5 kJ @525 K | −37 kJ @525 K |
|  | Heat capacity $H_2$, 3 mole, 293 → 525 K | −27 kJ @525 K |  |
| Heat (B) | Reaction heat | 141 kJ @525 K | 208 kJ @525 K |
|  | Condensation heat $CH_3OH$, 1 mole | 28 kJ @375 K |  |
|  | Condensation heat $H_2O$, 1 mole | 39 kJ @375 K |  |

In this embodiment step b. produces (208−37)=171 kJ/mole of converted $CO_2$. As in Example 1, the energy produced by step b. is more than the energy required for step a.

Thus, the invention has been described by reference to certain embodiments discussed above. It will be recognized that these embodiments are susceptible to various modifications and alternative forms well known to those of skill in the art.

Many modifications in addition to those described above may be made to the structures and techniques described herein without departing from the spirit and scope of the invention. Accordingly, although specific embodiments have been described, these are examples only and are not limiting upon the scope of the invention.

What is claimed is:
1. An energy integrated $CO_2$ conversion process comprising the steps of
   a. a $CO_2$ enrichment step whereby the $CO_2$ concentration of a feed gas is increased, said enrichment step requiring an energy input;
   b. a $CO_2$ conversion step whereby $CO_2$ is converted to a liquid product, said conversion step producing an energy output;

whereby the energy output is used to at least partially offset the energy input,
wherein the feed gas is ambient air, and wherein step a. is operated at a temperature in a range of from 250K to 450K,
wherein step b. produces from 100 kJ to 200 kJ per mole of converted $CO_2$.

2. The process of claim 1 wherein step a. comprises a swing absorption/desorption process.

3. The process of claim 2 wherein the swing process comprises a temperature swing, a pressure swing, a moisture swing, or a combination thereof.

4. The process of claim 1, wherein step a. comprises use of an absorbent comprising an alkali metal salt or an alkaline earth salt.

5. The process of claim 4 wherein the absorbent comprises a salt of sodium or potassium.

6. The process of claim 5 wherein the absorbent comprises potassium carbonate hydrate.

7. The process of claim 1, wherein step b. comprises conversion of $CO_2$ to methanol.

8. The process of claim 7 wherein step b. comprises a thermo-catalytic conversion of $CO_2$ to methanol.

9. The process of claim 7 wherein step b. is carried out in a reactor, and equilibrium shift is accomplished by condensing methanol inside the reactor.

10. The process of claim 9 wherein the reactor comprises at least one reaction zone and at least one methanol condensation zone, the reaction zone or zones having a higher temperature than the methanol condensation zone or zones.

11. The process of claim 10 wherein the reaction zone or zones have the same pressure as the condensation zone or zones.

12. The process of claim 1 wherein step a. comprises a temperature swing of 60K to 150K.

13. The process of claim 12 wherein step a. comprises a temperature swing of 60K to 99K.

14. The process of claim 1, wherein step b. is operated at temperatures in a range of from 425K to 550K.

* * * * *